(12) United States Patent
Ting et al.

(10) Patent No.: US 11,241,173 B2
(45) Date of Patent: Feb. 8, 2022

(54) PHYSIOLOGICAL MONITORING SYSTEMS AND METHODS OF ESTIMATING VITAL-SIGN DATA

(71) Applicant: MEDIATEK INC., Hsinchu (TW)

(72) Inventors: Yuan-Wen Ting, Hsinchu (TW); Yu-Ting Liu, Hsinchu (TW); Chih-Ming Fu, Hsinchu (TW); Che-Kuang Lin, Hsinchu (TW)

(73) Assignee: MEDIATEK INC., Hsinchu (TW)

( * ) Notice: Subject to any disclaimer, the term of this patent is extended or adjusted under 35 U.S.C. 154(b) by 0 days.

(21) Appl. No.: 16/924,457

(22) Filed: Jul. 9, 2020

(65) Prior Publication Data
US 2022/0007971 A1   Jan. 13, 2022

(51) Int. Cl.
*A61B 5/1172* (2016.01)
*A61B 5/1171* (2016.01)
*G16H 50/30* (2018.01)
*G06K 9/46* (2006.01)
*A61B 5/0205* (2006.01)
*G06K 9/00* (2006.01)

(52) U.S. Cl.
CPC .......... *A61B 5/1172* (2013.01); *A61B 5/0205* (2013.01); *A61B 5/1176* (2013.01); *G06K 9/00885* (2013.01); *G06K 9/46* (2013.01); *G16H 50/30* (2018.01); *G06K 2009/00939* (2013.01)

(58) Field of Classification Search
CPC .......................... G06K 9/00013; G06K 9/2027
See application file for complete search history.

(56) References Cited

U.S. PATENT DOCUMENTS

| | | | | |
|---|---|---|---|---|
| 11,003,798 | B1* | 5/2021 | Mhaske | G06F 21/32 |
| 11,070,550 | B2* | 7/2021 | Rahmel | H04W 12/065 |
| 2016/0070967 | A1* | 3/2016 | Du | G06T 7/32 |
| | | | | 382/124 |
| 2016/0132711 | A1* | 5/2016 | Setterberg | G06K 9/00926 |
| | | | | 382/124 |

(Continued)

FOREIGN PATENT DOCUMENTS

CN   101593268 A   12/2009
CN   105809178 A   7/2016
(Continued)

OTHER PUBLICATIONS

Chinese language office action dated Dec. 6, 2021, issued in application No. TW 110124695.

*Primary Examiner* — John B Strege
(74) *Attorney, Agent, or Firm* — McClure, Qualey & Rodack, LLP

(57) ABSTRACT

A physiological monitoring system is provided. The physiological monitoring system includes a feature extraction device, an identifier, a processor, a physiological sensing device, and a vital-sign detector. The feature extraction device extracts biological information of an object to generate an extraction signal. The identifier receives the extraction signal and verifies an identity of the object according to the extraction signal. The processor receives the extraction signal and obtains at least one biological feature of the user according to the extraction signal. The physiological sensing device senses a physiological feature to generate a bio-signal. The vital-sign detector estimates vital-sign data of the object according to the bio-signal and the at least one biological feature.

18 Claims, 6 Drawing Sheets

(56) References Cited

U.S. PATENT DOCUMENTS

| | | | | |
|---|---|---|---|---|
| 2016/0203354 | A1* | 7/2016 | Choi | G06K 9/001 |
| | | | | 382/124 |
| 2018/0315063 | A1* | 11/2018 | Cheesman | A61B 5/0205 |
| 2019/0362120 | A1* | 11/2019 | Yeke Yazdandoost | ...... |
| | | | | H01L 27/14629 |
| 2020/0405158 | A1* | 12/2020 | Jeong | G16H 20/30 |
| 2021/0106283 | A1* | 4/2021 | Zhong | A61B 5/02427 |

FOREIGN PATENT DOCUMENTS

| | | |
|---|---|---|
| CN | 206236087 U | 6/2017 |
| CN | 109770881 A | 5/2019 |
| CN | 110738998 A | 1/2020 |
| CN | 111199276 A | 5/2020 |

\* cited by examiner

PHYSIOLOGICAL MONITORING SYSTEMS AND METHODS OF ESTIMATING VITAL-SIGN DATA

BACKGROUND OF THE INVENTION

Field of the Invention

The invention relates to a physiological monitoring system, and more particularly to a physiological monitoring system which detects vital-sign data of a user based on the biological information about the personal identification of the user.

Description of the Related Art

With aging societies, more and more burden is placed on hospital resources. Moreover, cardiovascular diseases are increasing, as people age and stress increases for modern day living. Thus, vital-sign self-measurement devices have become an important target for development in the healthcare industry. Through sensing or detecting medically health information, such as electrocardiography (ECG), photoplethysmogram (PPG), heart rate, and blood pressure of patients in bio-signal self-measurement manners, the patients can monitor their own physiology status anytime, to relieve strain on hospital resources and provide needed medical attention to patients. Generally, to enhance the accuracy of a vital-sign self-measurement device, a user needs to input his/her biological features, such as age, gender, weight, height, and race, such that the vital-sign self-measurement device can select an appropriate model or adjust parameters of a reference model to estimate the user's health information. However, some biological features, such as the age, weight, and height, may change over time, and the user has to update these biological features every once in a while, which is inconvenient, especially for the elderly. In some situations, one vital-sign self-measurement device is shared by several users, such as a family. Since these users may be of different ages, genders, weight, height, or races, the appropriate models for estimating the health information are also different. Every time the vital-sign self-measurement device operates to estimate one of these users, the user has to manually switch the vital-sign self-measurement device to an appropriate model, which is inconvenient and is also easy to switch to the wrong model.

BRIEF SUMMARY OF THE INVENTION

Thus, it is desired to provide a physiological monitoring system which detects vital-sign data of a user based on biological features which is obtained from information about the personal identification of the user, thereby enhancing the accuracy of the detection result.

An exemplary embodiment of a physiological monitoring system is provided. The physiological monitoring system comprises a feature extraction device, an identifier, a processor, a physiological sensing device, and a vital-sign detector. The feature extraction device extracts biological information of an object to generate an extraction signal. The identifier receives the extraction signal and verifies an identity of the object according to the extraction signal. The processor receives the extraction signal and obtains at least one biological feature of the user according to the extraction signal. The physiological sensing device senses a physiological feature to generate a bio-signal. The vital-sign detector estimates vital-sign data of the object according to the bio-signal and the at least one biological feature.

An exemplary embodiment of a method of estimating vital-sign data. The method comprises the steps of extracting biological information of an object to generate an extraction signal for verifying an identity of the object; obtaining at least one biological feature of the user according to the extraction signal; sensing a physiological feature to generate a bio-signal; and estimating vital-sign data of the object according to the bio-signal and the at least one biological feature.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated model of carrying out the invention. This description is made for the purpose of illustrating the general principles of the invention and should not be taken in a limiting sense. The scope of the invention is best determined by reference to the appended claims.

Figure 1:
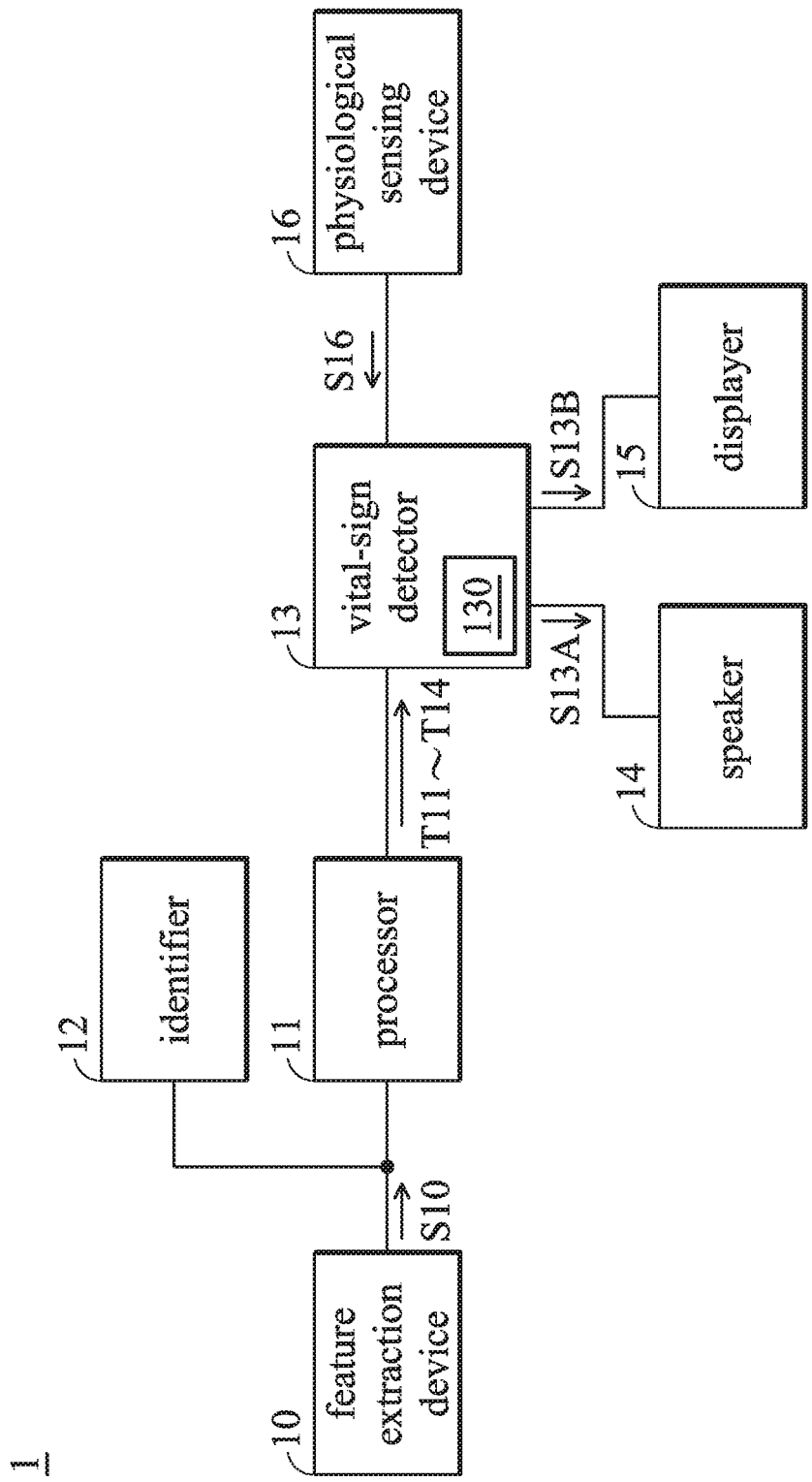
FIG. 1 shows one exemplary embodiment of a physiological monitoring system.
Figure 2:
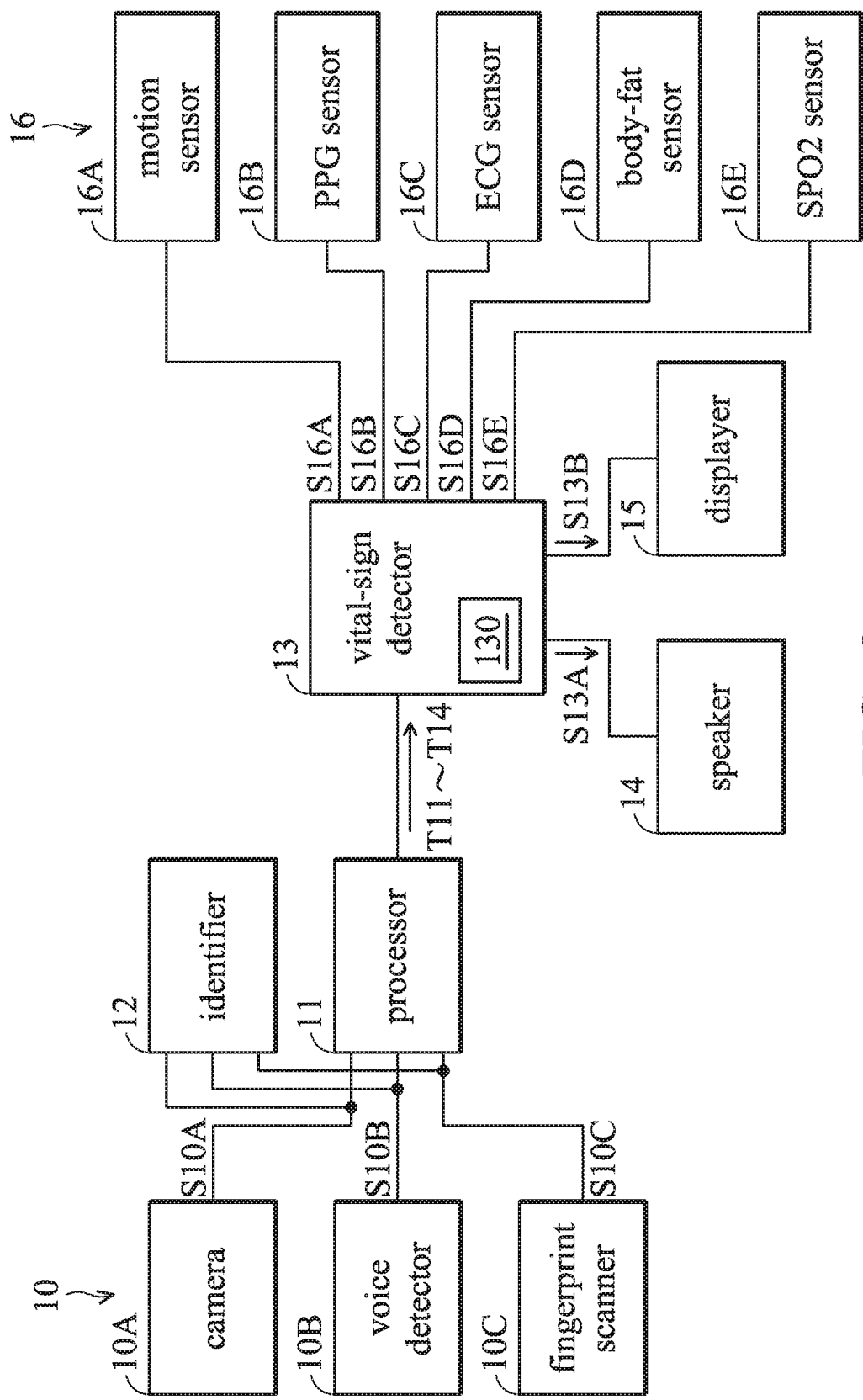
FIG. 2 shows another exemplary embodiment of a physiological monitoring system.

FIG. 1 shows one exemplary embodiment of a physiological monitoring system. As shown in FIG. 1, a physiological monitoring system 1 is provided to operate to monitor at least one vital-sign of an object, such as a user, to generate vital-sign data. The physiological monitoring system 1 comprises a feature extraction device 10, a processor 11, an identifier 12, a vital-sign detector 13, a speaker 14, a displayer 15, and a physiological sensing device 16. In an embodiment, the feature extraction device 10 operates to extract the biological information of the user to generate at least one extraction signal S10. The extracted biological information of the user comprises the facial profile, a fingerprint, and/or voiceprint which are unique to the user. In an embodiment, as shown in FIG. 2, the feature extraction device may comprise a camera 10A, a voice detector 10B, and a fingerprint scanner 10C. The camera 10A captures an image of the face of the user which is facing the camera 10A and generates an extraction signal S10A according to the captured image. In an embodiment, the camera 10A may be a TrueDepth camera. The extraction signal S10A comprises data related to the facial profile of the user. The voice detector 10B detects sound transmitted from the user. The voice detector 10B analyzes the features of the detected sound to obtain the voiceprint of the user and generates an extraction signal S10B according to the obtained voiceprint. In an embodiment, the voice detector 10B comprises a microphone to receive sound. The fingerprint scanner 10C scans an image of one finger of the user which is contacting a touch panel of the fingerprint scanner 10C, such as the fingerprint of the right thumb. The fingerprint scanner 10C analyzes scanned the scanned image and detects the fingerprint of the finger, and generates an extraction signal 10C according to the detected fingerprint. The touch panel of the fingerprint scanner 10C is dedicated for fingerprint scanning on a portion of a touch screen. The camera 10A, the voice detector 10B, and the fingerprint scanner 10C operate at different times. Alternatively, at least two of camera 10A, the voice detector 10B, and the fingerprint scanner 10C operate at the same time.

Since the facial profile, the fingerprint, and the voiceprint are unique to the user, the identifier 12 can verify the identity of the user according to at least one of the extraction signals S10A~S10C. In the cases where the physiological monitoring system 1 is in a locked mode, the identifier 12 unlocks the physiological monitoring system 1 when the identity of the user is verified successfully. In other cases, the identifier 12 can determine the authority of the user to access the physiological monitoring system 1 based the verified identify. In the embodiment, the identifier 12 may use any biometrics manners to verify the identity of the user according to at least one of the extraction signals S10A~S10C.

Referring to FIGS. 1-2, the processor 11 also receives at least one of the extraction signals S10A~S10C and obtains at least one biological feature of the user according to the received extraction signal(s). Generally, a person's age, gender, body information (including weight and height), and race can be learned from the facial profile. Thus, in the embodiment, when the camera 10A operates to capture an image of the face of the user, the processor 11 receives the extraction signal S10A which comprises the data related to the facial profile of the user and analyzes the extraction signal S10A to obtain at least one of the age, the gender, the body information, and the race of the user as at least one biological feature. After obtaining the at least one biological feature, the processor 11 generates at least one corresponding bio-tag for the vital-sign detector 13. In the embodiment, the bio-tags related to the age, the gender, the body information, and the race are represented by T11~T14, respectively. Since the bio-tags T11~T14 are derived from the biological information of the user, one bio-tag or a combination of at least two bio-tags serves as an identification of the user.

Moreover, a person's age and gender can be learned from his/her voiceprint. Thus, in the embodiment, when the voice detector 10B detects sound transmitted from the user, the processor 11 receives the extraction signal S10B and analyzes the extraction signal S10B to obtain at least one of the age and the gender of the user as at least one biological feature. After obtaining the at least one biological feature, the processor 11 generates at least one corresponding bio-tag T11 or T12 for the vital-sign detector 13.

Generally, as people age, the fingerprints of the fingers become shallower. Thus, a person's age or age range can be learned from his/her fingerprint. In the embodiment, when the fingerprint scanner 10C detects the fingerprint of one finger of the user, the processor 13 receives the extraction signal S10C and analyzes the extraction signal S10C to obtain the age or the age range of the user as a biological feature. After obtaining the biological feature, the processor 11 generates a corresponding bio-tag T11 for the vital-sign detector 13.

The physiological sensing device 16 operates to sense at least one physiological feature of the user who is wearing, holding or contacting the physiological sensing device 16, such as the motion, photoplethysmogram (PPG), electrocardiography (ECG), the body fat, and amount of red light (R) and infrared (IR) received by the blood of the user. The physiological sensing device 16 generates at least one bio-signal according to the at least one sensed physiological feature. Referring to FIG. 2, in an embodiment, the physiological sensing device 16 comprises a motion sensor 16A, a photoplethysmogram (PPG) sensor 16B, an electrocardiography (ECG) sensor 16C, a body-fat sensor 16D, and a SPO2 sensor 16E. The motion sensor 16A is disposed on a specific portion of the body of the user, such as one arm, one wrist, or one leg of the user, to sense the motion or activity of the user and generate a bio-signal S16A. The PPG sensor 16B illuminates the skin of the user (for example, the skin of the right wrist) by a red light (R) source, a green light (G) source, or infrared (IR) source, detects the changes in light absorption of the blood under the skin, and generates a bio-signal S16B based on the measured changes. The ECG sensor 16C senses the electrical activity of the heart of the user through electrodes contacting the skin of the user and generates a bio-signal S16C. The body-fat sensor 16D provides a small electric current to the body of the user through two conductors attached to the body and measures the resistance between the two conductors to generate a bio-signal S16D.

The SPO2 sensor 16E comprises a probe, such as a clip-type probe. The clip-type probe grips a specific portion of the body of the user, such as the right index finger of the user. A red light (R) source and an infrared (IR) source are disposed on one side of the probe, and a photo detector is disposed on the other side thereof. The light emitted by the R and IR sources travels through the tissue and blood and is then collected in the photo detector. The photo detector generates a bio-signal S16E according to the amount of received R and IR. Since the deoxyhemoglobin (Hb) and the oxyhemoglobin (HbO2) in the blood have different capacities for R and IR having different wavelengths, the bio-signal S16E is related to the amount of the deoxyhemoglobin (Hb) and the amount of the oxyhemoglobin (HbO2) in the blood.

In the above embodiment, the processor 11 receives at least one of the extraction signals S10A~S10C indicating at least one biological feature and generates at least one bio-tag according to the received extraction signal(s). In another embodiment, the processor 11 further receives at least one of the bio-signals S16A~S16E and generates at least one bio-tag according to the received extraction signal(s) and the received bio-signal(s). In this embodiment, since the bio-signals S16A~S16E indicate the physiological features of the user, the bio-tag(s) indicating the biological feature(s) of the user can be determined more accurately when at least one bio-signal is also considered.

The vital-sign detector 13 receives the bio-tag(s) from the processor 11 and the bio-signal(s) from the physiological sensing device 16 and detects vital-sign data of the user according to the received the bio-tag(s) and the received bio-signal(s). In the embodiment, the vital-sign data comprises at least one of an index representing an obstructive sleep apnea (OSA) risk, a blood pressure, a body-fat percentage, an index representing an incidence of cardiovascular diseases, an index representing a sleep stage, a value representing a heart rate, an index representing heart rate variability, an index representing atrial fibrillation, and a value representing blood oxygen saturation. As described above, the bio-tags represent the different biological features, such as the age, the gender, the body information, and the race. In the embodiment, the vital-sign detector 13 can select an appropriate estimation model or change parameters of a reference estimation model according to at least one bio-tag, so that the vital-sign detector 13 can accurately estimate vital-sign data of the user.

Figure 3:
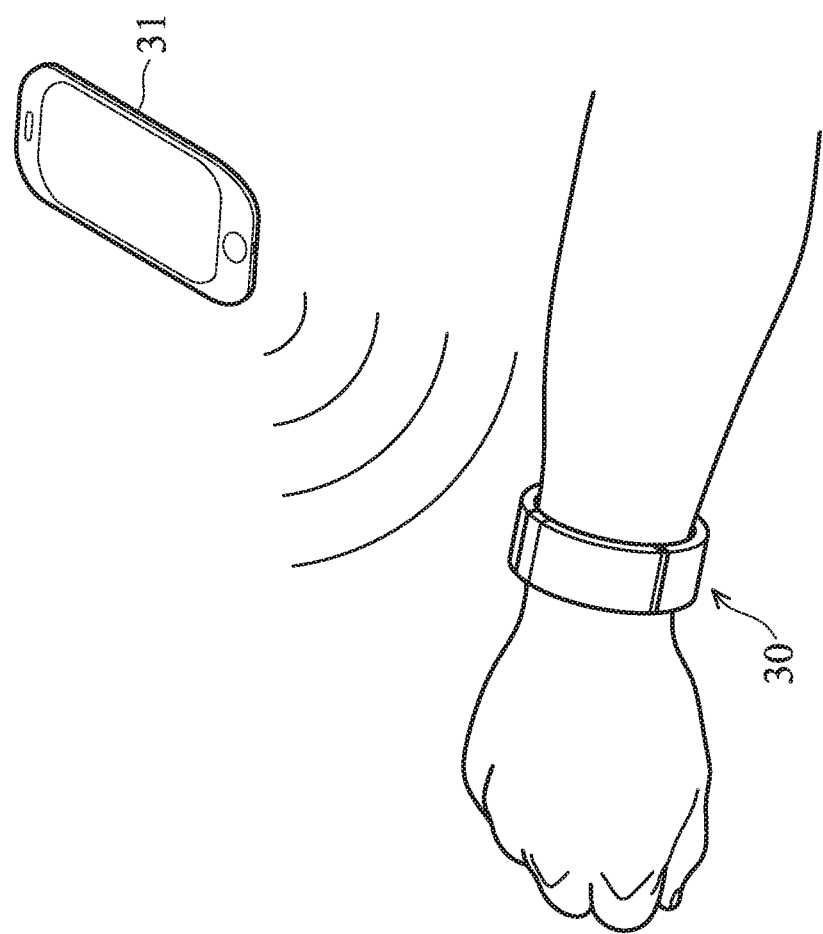
FIG. 3 shows another exemplary embodiment of a physiological monitoring system.

In an embodiment, the physiological monitoring system 1 is implemented in an apparatus, such as a physiological monitoring apparatus or a smart phone. In another embodiment, the physiological monitoring system 1 is implemented in different apparatuses. As shown in FIG. 3, there are a smart phone 30 and a wearable device 31 with healthcare functions, such as a smart watch. In this embodiment, the feature extraction device 10, the processor 11, and the identifier 12 are disposed in the smart phone 30, while the vital-sign detector 13, the speaker 14, the displayer 15, and the physiological sensing device 16 are disposed in the smart watch 31. The smart phone 30 transmits the bio-tags to the smart watch 31 in a wireless manner.

In the following paragraphs, the detail of the operation of the vital-sign detection device 13 will be described with reference to several embodiments.

According to an embodiment, the vital-sign detection device 13 stores a plurality of estimation models for cardiovascular diseases in the memory 130. When vital-sign detection device 13 receives at least one of the bio-tags T11~T14, such as the bio-tag (age) T11 and the bio-tag (gender) T12, and further receives the bio-signal S16C, the vital-sign detection device 13 selects one estimation model from the memory 130 according to the received bio-tags T11 and T12 and then estimates an index representing an incidence of cardiovascular diseases according to the bio-signal S16C related to the electrical activity of the heart by using the selected estimation model. The estimated index may be transmitted to the displayer 15 through a corresponding image signal S13B and shown on the displayer 15.

In an embodiment where the user which is wearing, holding or contacting the physiological sensing device 16 is sleeping, when the vital-sign detection device 13 receives at least one of the bio-tags T11~T14 and further receives the bio-signals S16A and S16B, the vital-sign detection device 13 selects one estimation model from the memory 130 according to the received bio-tag(s) and then estimates an index representing a sleep stage of the user according to the bio-signals S16A and S16B by using the selected estimation model. The estimated index may be transmitted to the displayer 15 through a corresponding image signal S13B and shown on the displayer 15.

In another embodiment, when the vital-sign detection device 13 receives at least one of the bio-tags T11~T14 and further receives at least one of the bio-signals S16B~S16C, the vital-sign detection device 13 selects one estimation model from the memory 130 according to the received bio-tag(s) and then estimates a value representing the heart rate of the user or an index representing the heart rate variability of the user according to the at least one of the bio-signals S16B~S16C by using the selected estimation model. The estimated value or index may be transmitted to the displayer 15 through a corresponding image signal S13B and shown on the displayer 15.

In an embodiment, when the vital-sign detection device 13 receives at least one of the bio-tags T11~T14 and further receives the bio-signals S16A~S16B, the vital-sign detection device 13 selects one estimation model from the memory 130 according to the received bio-tag(s) and then estimates an index representing the atrial fibrillation of the user according to the bio-signals S16A~S16B by using the selected estimation model. In another embodiment, an index representing the atrial fibrillation of the user can be estimated according to the bio-signal S16C. In detail, when the vital-sign detection device 13 receives at least one of the bio-tags T11~T14 and further receives the bio-signal S16C, the vital-sign detection device 13 selects one estimation model from the memory 130 according to the received bio-tag(s) and then estimates an index representing the occurrence of the atrial fibrillation on the user according to the bio-signal S16C by using the selected estimation model. The estimated index may be transmitted to the displayer 15 through a corresponding image signal S13B and shown on the displayer 15.

In an embodiment, when the SPO2 is connecting through the probe, when the vital-sign detection device 13 receives at least one of the bio-tags T11~T14 and further receives the bio-signal S16D, the vital-sign detection device 13 selects one estimation model from the memory 130 according to the received bio-tag(s) and then estimates a value representing the blood oxygen saturation (SPO2) according to the bio-signal S16D by using the selected estimation model. The estimated value may be transmitted to the displayer 15 through a corresponding image signal S13B and shown on the displayer 15.

Figure 4:
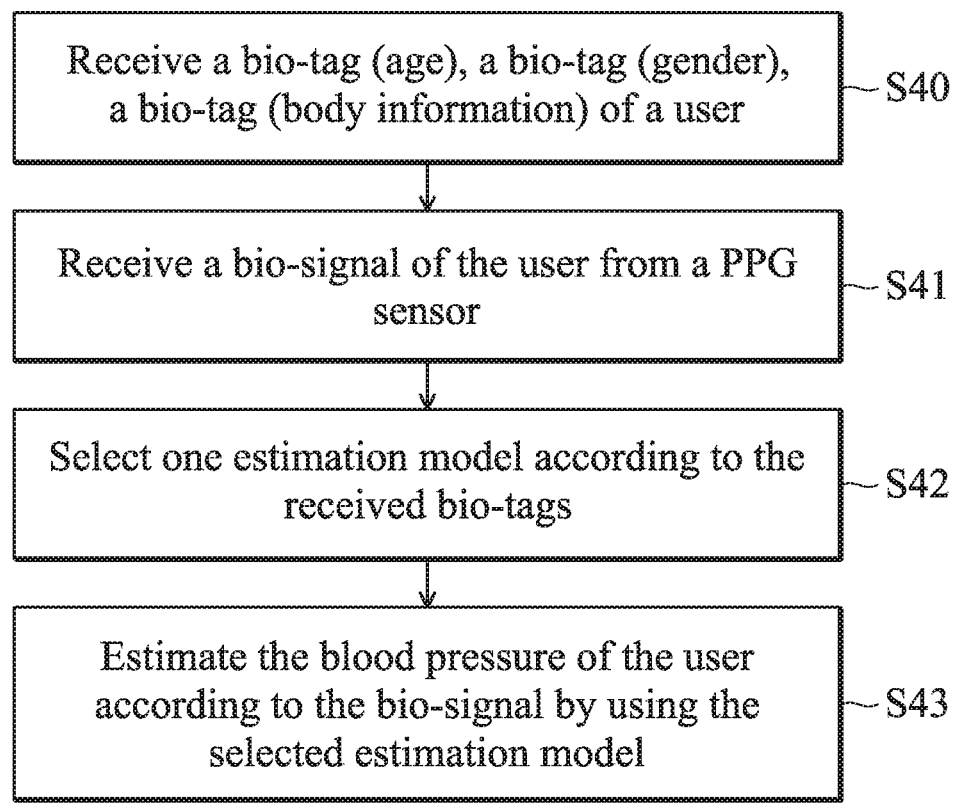
FIG. 4 shows a flow chart of estimating a blood pressure according to the bio-signal(s) and bio-tag(s) according to an exemplary embodiment.

FIG. 4 shows a flow chart of estimating a blood pressure according to the bio-signal(s) and bio-tag(s) according to an exemplary embodiment. The vital-sign detection device 13 stores a plurality of estimation models for blood pressures in the memory 130. When vital-sign detection device 13 receives at least one of the bio-tags T11~T14 (step S40), such as the bio-tag (age) T11, the bio-tag (gender) T12, the bio-tag (body information) T13, and further receives the bio-signal S16B from the PPG sensor 16B (step S41), the vital-sign detection device 13 selects one estimation model from the memory 130 according to the received bio-tags T11~T13 (step S42) and then estimates the blood pressure according to the bio-signal S16B by using the selected estimation model (step S43). The value of the blood pressure may be transmitted to the displayer 15 through an image signal S13B and shown on the displayer 15. According to another embodiment, the memory 130 may store historical estimation models which were used in the previous estimation of the blood pressures of different users. In this embodiment, at the step S42, the vital-sign detection device 13 reads the historical estimation model for the previous estimation of the blood pressure of the user from the memory 130 according to the bio-tags T11~T13.

Figure 5:
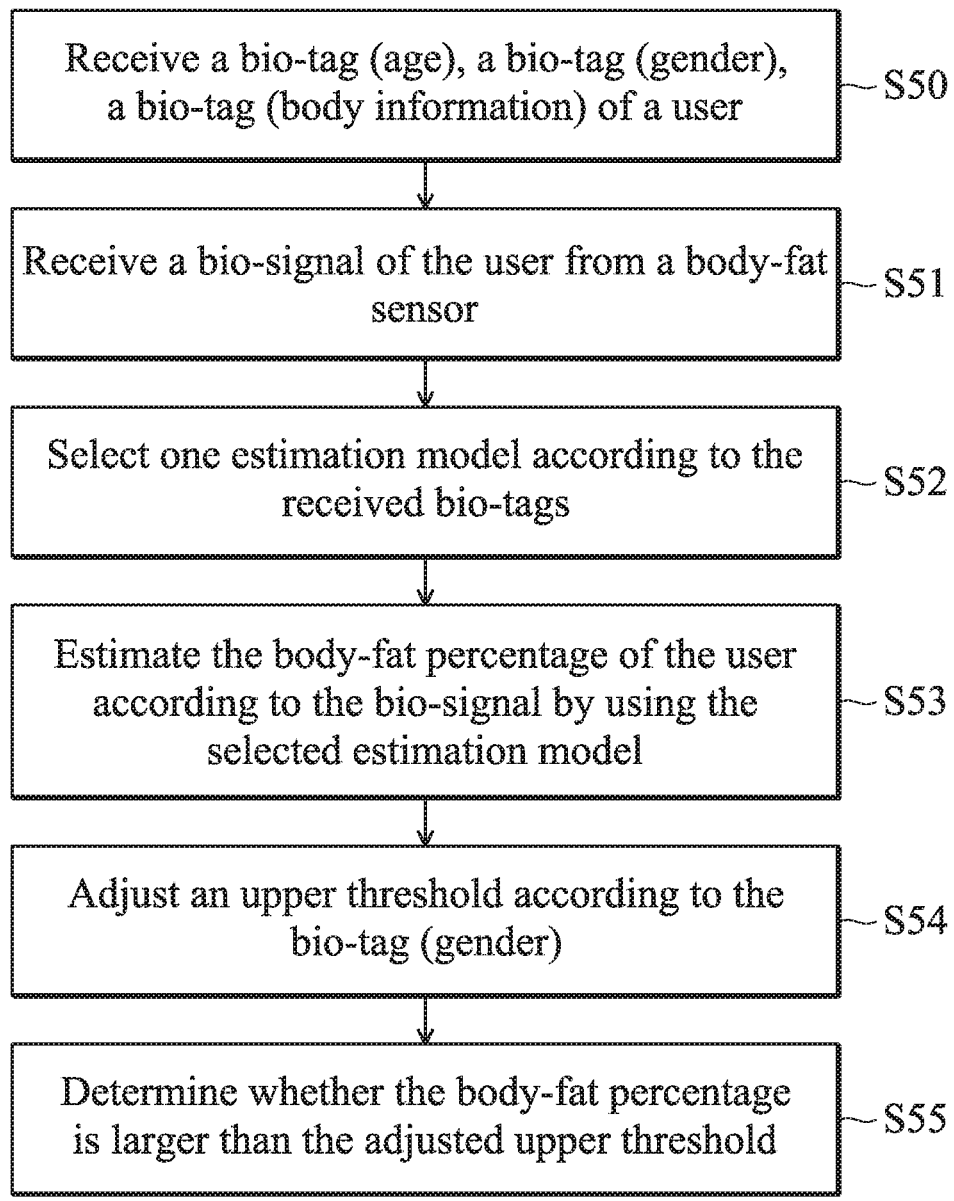
FIG. 5 shows a flow chart of estimating a body-fat percentage according to the bio-signal(s) and bio-tag(s) according to an exemplary embodiment.

FIG. 5 shows a flow chart of estimating a body-fat percentage according to the bio-signal(s) and bio-tag(s) according to an exemplary embodiment. In an embodiment, the vital-sign detection device 13 stores a plurality of estimation models for body-fat percentages in the memory 130. When vital-sign detection device 13 receives at least one of the bio-tags T11~T14 (step S50), such as the bio-tag (age) T11, the bio-tag (gender) T12, the bio-tag (body information) T13, and further receives the bio-signal S16D from the body-fat sensor 16D (step S51), the vital-sign detection device 13 selects one estimation model from the memory 130 according to the received bio-tags T11~T13 (step S52) and then estimates the body-fat percentage according to the bio-signal S16C by using the selected estimation model (step S53). The value of the body-fat percentage may be transmitted to the displayer 15 through an image signal S13B and shown on the displayer 15. After estimating the body-fat percentage, the vital-sign detection device 13 adjusts an upper threshold of a normal range according to the bio-tag (gender) T12 (step S54). The vital-sign detection device 13 determines whether the body-fat percentage is larger than the adjusted upper threshold (step S55). In response to determining that the body-fat percentage is larger than the adjusted upper threshold, the vital-sign detection device 13 generates a control signal S13A to control the speaker 14 to play a warning sound.

Figure 6:
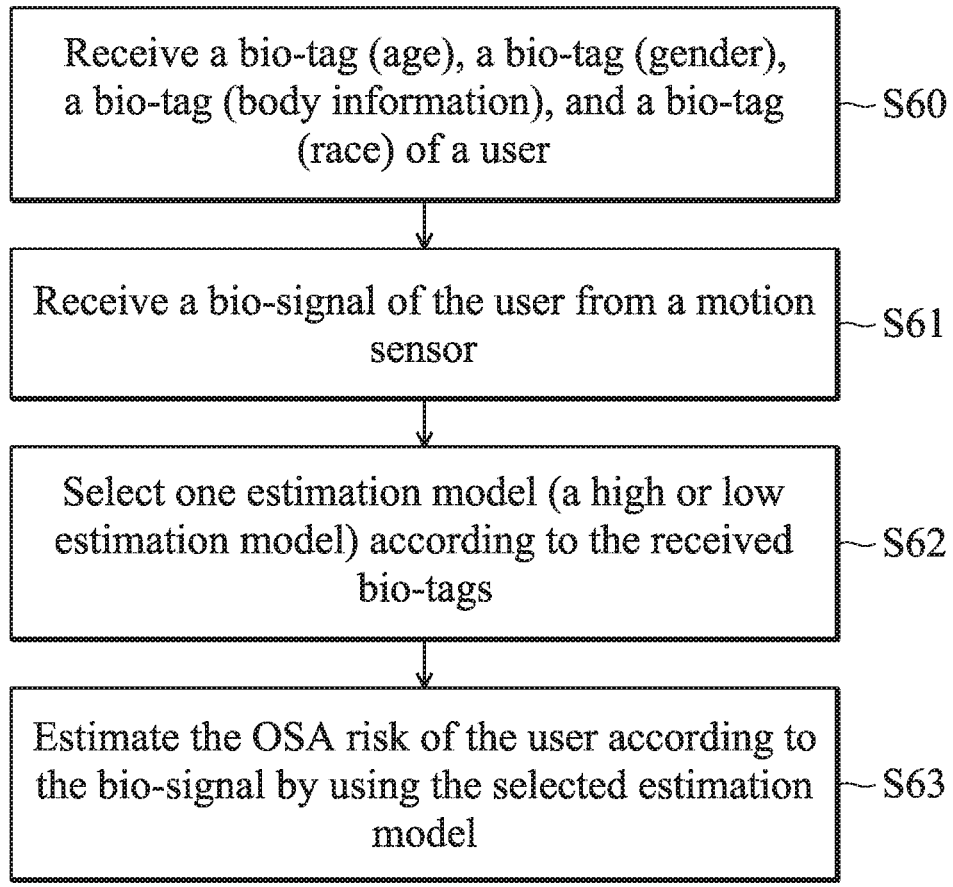
FIG. 6 shows a flow chart of estimating an OSA risk according to the bio-signal(s) and bio-tag(s) according to an exemplary embodiment.

FIG. 6 shows a flow chart of estimating an OSA risk according to the bio-signal(s) and bio-tag(s) according to an exemplary embodiment. In an embodiment, the vital-sign detection device 13 stores a plurality of estimation models for OSA risks in the memory 130. When vital-sign detection device 13 receives at least one of the bio-tags T11~T14 (step S60), such as the bio-tag (age) T11, the bio-tag (gender) T12, the bio-tag (body information) T13, and the bio-tag (race) T14, and further receives the bio-signal S16A from the motion sensor 16A (step S61), the vital-sign detection device 13 selects one estimation model from the memory 130 according to the received bio-tags T11~T14 (step S62). For example, when the bio-tag (age) T11 indicates that the age of the user is more than 40 years old, the bio-tag (gender) T12 indicate that the user is a male, the bio-tag (body information) T13 indicates that the weight of the user is great, and the bio-tag (race) T14 indicates that the user is an Asian, the vital-sign detection device 13 selects a high-risk estimation model which includes a lower threshold. In other cases, the vital-sign detection device 13 may selects a low-risk estimation model. The vital-sign detection device 13 then estimates the OSA risk according to the bio-signal S16A by using the selected estimation model (step S63). The value of the vital-sign detection device 13 may be transmitted to the displayer 15 through an image signal S13B and shown on the displayer 15. After estimating the body-fat percentage, the vital-sign detection device 13 determines whether the OSA risk is larger than the threshold of the selected estimation model. In response to determining that the OSA risk is larger than the threshold, the vital-sign detection device 13 generates a control signal S13A to control the speaker 14 to play a warning sound.

According to an embodiment, the memory 130 may store databases of different users. Each database comprises the historical estimation models and/or the historical parameters which were used in the previous estimation of the vital-sign data of a user and further comprises the historical vital-sign data which was estimated in the previous estimation. When the physiological monitoring system 1 operates to estimate vital-sign data of a user, the vital-sign detection device 13 may access a database exclusive to the user from the memory 130 according to at least one bio-tag of the user. Thus, the user can estimate vital-sign data by referring to the historical estimation model or parameters and by taking the historical vital-sign data as reference data, thereby enhancing of the accuracy of the estimation of the vital-sign data. Moreover, each time the vital-sign detection device 13 estimates vital-sign data of a user, the vital-sign detection device 13 stores the estimated vital-sign data into a database exclusive to the user which is determined according to at least one bio-tag of the user.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A physiological monitoring system comprising:
   a feature extraction device extracting biological information of an object to generate an extraction signal;
   an identifier receiving the extraction signal and verifying an identity of the object according to the extraction signal;
   a processor receiving the extraction signal and obtaining at least one biological feature of the user according to the extraction signal;
   a physiological sensing device sensing a physiological feature to generate a bio-signal; and
   a vital-sign detector estimating vital-sign data of the object according to the bio-signal and the at least one biological feature, wherein the vital-sign detector determines whether a value of the vital-sign data of the object is in a range, and at least one threshold of the range is determined according to the at least one biological feature.

2. The physiological monitoring system as claimed in claim 1, wherein the biological information of the object comprises at least one of a facial profile, fingerprint, and voice of the object.

3. The physiological monitoring system as claimed in claim 1, wherein the feature extraction device comprises:
   a camera capturing an image of a portion of a body of the object and generates the extraction signal according to the captured image.

4. The physiological monitoring system as claimed in claim 3 wherein the processor analyzes the extraction signal to obtain at least one of age, gender, a body information, and race of the object as the at least one biological feature.

5. The physiological monitoring system as claimed in claim 1, wherein the extraction device comprises:
   a voice detector detecting sound from the object and generating the extraction signal according to the detected sound.

6. The physiological monitoring system as claimed in claim 5, wherein the processor analyzes the extraction signal to obtain at least one of age and gender of the object as the at least one biological feature.

7. The physiological monitoring system as claimed in claim 1, wherein the extraction device comprises:
   a fingerprint scanner detecting a fingerprint of the object and generating the extraction signal according to the detected fingerprint.

8. The physiological monitoring system as claimed in claim 7, wherein the processor analyzes the extraction signal to obtain age of the object as the at least one biological feature.

9. The physiological monitoring system as claimed in claim 1, wherein the vital-sign detector stores a plurality of estimation models, and the vital-sign detector selects one estimation model from the plurality of estimation models according to the at least one biological feature and estimates the vital-sign data of the object according to the bio-signal by using the selected estimation model.

10. The physiological monitoring system as claimed in claim 1, wherein the vital-sign detector estimates the vital-sign data of the object according to the bio-signal by using an estimation model, and at least one of parameters of the estimation model is determined according to the at least one biological feature.

11. The physiological monitoring system as claimed in claim 1, wherein the physiological sensing device comprises at least one of a motion sensor, a photoplethysmogram (PPG) sensor, an electrocardiography (ECG) sensor, and a body-fat sensor.

12. The physiological monitoring system as claimed in claim 1, wherein the vital-sign data comprises at least one of an index representing an obstructive sleep apnea (OSA) risk, a blood pressure, a body-fat percentage, an index representing an incidence of cardiovascular diseases, an index representing a sleep stage, a value representing a heart rate, an index representing heart rate variability, an index representing atrial fibrillation, and a value representing blood oxygen saturation.

13. A method of estimating vital-sign data comprising:
  extracting biological information of an object to generate an extraction signal for verification of an identity of the object;
  obtaining at least one biological feature of the user according to the extraction signal;
  sensing a physiological feature to generate a bio-signal;
  estimating vital-sign data of the object according to the bio-signal and the at least one biological feature;
  determining whether a value of the vital-sign data of the object is in a range; and
  determining at least one threshold of the range according to the at least one biological feature.

14. The method of estimating vital-sign data as claimed in claim 13, wherein the biological information of the object comprises at least one of a facial profile, fingerprint, and voice of the object.

15. The method of estimating vital-sign data as claimed in claim 13, wherein estimating the vital-sign data comprising:
  storing a plurality of estimation models;
  selecting one estimation model from the plurality of estimation models according to the at least one biological feature; and
  estimating the vital-sign data of the object according to the bio-signal by using the selected estimation model.

16. The method of estimating vital-sign data as claimed in claim 13, wherein estimating the vital-sign data comprising:
  estimating the vital-sign data of the object according to the bio-signal by using an estimation model; and
  determining at least one of parameters of the estimation model according to the at least one biological feature.

17. The method of estimating vital-sign data as claimed in claim 13, wherein the biological information of the object is extracted by at least one of a motion sensor, a photoplethysmogram (PPG) sensor, an electrocardiography (ECG) sensor, and a body-fat sensor.

18. The method of estimating vital-sign data as claimed in claim 13, wherein the vital-sign data comprises at least one of an index representing an obstructive sleep apnea (OSA) risk, a blood pressure, a body-fat percentage, an index representing an incidence of cardiovascular diseases, an index representing a sleep stage, a value representing a heart rate, an index representing heart rate variability, an index representing atrial fibrillation, and a value representing blood oxygen saturation.

* * * * *